(12) United States Patent
Kuo

(10) Patent No.: US 7,679,393 B2
(45) Date of Patent: Mar. 16, 2010

(54) TESTING APPARATUS FOR FIXING AND TESTING A LCD PANEL

(76) Inventor: Shun-Kun Kuo, 4F., No. 6, Lane 195, Sec. 4, Singling Rd., Wunshan District, Taipei City (TW)

( * ) Notice: Subject to any disclaimer, the term of this patent is extended or adjusted under 35 U.S.C. 154(b) by 158 days.

(21) Appl. No.: 12/118,813

(22) Filed: May 12, 2008

(65) Prior Publication Data

US 2009/0278563 A1 Nov. 12, 2009

(51) Int. Cl.
*G01R 31/02* (2006.01)
(52) U.S. Cl. .................. 324/770; 324/156; 324/158.1
(58) Field of Classification Search ............... None
See application file for complete search history.

(56) References Cited

U.S. PATENT DOCUMENTS 6,150,833 A * 11/2000 Lin et al. .................. 324/770
6,232,616 B1 * 5/2001 Chen et al. ............. 250/559.45
6,353,466 B1 * 3/2002 Park ............................ 349/58
6,362,884 B1 * 3/2002 Okahira et al. ............. 356/399

* cited by examiner

*Primary Examiner*—Vinh P Nguyen
(74) *Attorney, Agent, or Firm*—Chun-Ming Shih

(57) ABSTRACT

A testing apparatus for fixing and testing a LCD panel includes a location frame and an adjustable base for fixing a camera set. The location frame and the adjustable base are connected together via a holder set. The adjustable base is able to be adjusted a distance between the location frame on the holder set. The location frame includes a framework set with adjustable plates on the edges of the backside of the framework. The adjustable plates are adjusted according to different sizes of the LCD panels for placing LCD panels with different sizes. The LCD panel is supported by top-supporting devices on the backside of the framework and located at the backside of the framework. Each edge of the framework is set with a movable shade which is adjusted according to different sizes of the LCD panels for shading metal rims of the LCD panel. When the camera set takes pictures of the LCD panel, the boundaries of the screen area and the rims are clearly defined to make the testing module accurately test the defects of the LCD panel and to improve testing quality.

14 Claims, 10 Drawing Sheets

TESTING APPARATUS FOR FIXING AND TESTING A LCD PANEL

BACKGROUND OF THE INVENTION

1. Field of the Invention

The present invention relates to a testing apparatus for fixing and testing a LCD panel. More particularly, the present invention relates to a testing apparatus that is configured to fix the LCD panel onto a location frame, thus a camera can take identical size of image from time to time for quality comparison process executed by a testing module.

2. Descriptions of the Related Art

Generally, manufactured LCD panels comprise good products and bad products. To avoid the bad products from getting into the market and influence reputation of the manufacturer, quality-control people of the manufacturer screen out the bad LCD panels. Thus, the quality-control people play important role in manufacturing process.

Generally, during testing process, the quality-control people do things wrong as the following ways:

1. The quality-control people hold the LCD panel by hands, and check the defects of the LCD panel by eyes contact; therefore, asthenopia after a long time checking would result in inefficient quality control that influences quality of products.

2. Fine defects are not easy to be screened out by eyes contact, which results in high error testing result.

Thus it can be seen that the aforementioned modes still have many drawbacks and are not good in design, thus the aforementioned products need improvement.

The inventor considers improvement in view of the aforementioned drawbacks of the conventional testing methods, and develops the present invention of testing apparatus for fixing and testing a LCD panel after a long term of research.

SUMMARY OF THE INVENTION

The primary objective of the present invention is to provide a testing apparatus for fixing and testing a LCD panel. A to-be-tested LCD panel is fixed onto a location frame, a camera set on a base can be adjusted to take identical size of image of the LCD panel from time to time, and then the image is transferred to a testing module for quality comparison.

Another objective of the present invention is to provide a testing apparatus for fixing and testing a LCD panel. An adjustable plate is set on a location frame, thus the location frame is provided for fixing LCD panels with different sizes.

Another objective of the present invention is to provide a testing apparatus for fixing and testing a LCD panel. A movable shade is set inside the location frame, the movable shade is configured to shade the metal rims of the LCD panel to clearly define the boundaries of the screen area and the rims and to avoid confusion due to image of the metal rims when testing quality of products.

The testing apparatus for fixing and testing a LCD panel achieves the aforementioned objectives comprises a location frame, a holder set, a placement base, and an adjustable base. The location frame and the adjustable base are corresponding to each other and located at two terminals of the holder set. The placement base is set on the holder set and between the location frame and the adjustable base. The adjustable base is configured to move forward and backward along the holder set, in which a photographing apparatus is able to be fixed on the adjustable base. The location frame comprises a position base pivoted to a framework, and the framework can turn over downward from the position base and abut the position base to make the framework parallel with the holder set. Adjustable plates are set on the backside of edges of the framework; the adjustable plate is set with a location portion. By adjusting each adjustable plate to adjust distance, LCD panels with different sizes can be set on the testing apparatus. The LCD panel is held by the top-supporting device, thus, the LCD panel can be fixed on the backside of the framework when the framework stands up. A movable shade is set inside the edges of the framework. The movable shade is able to protrude outward or hide behind the framework. The movable shade is configured to shade the metal rims of the LCD panel to clearly define the boundaries of the screen area and the rims and to avoid confusion due to the metal rims of the LCD panel when a camera set takes a picture of the LCD panel. The confusion influences the testing module in accuracy of analyzing and comparing image quality of LCD panel.

These features and advantages of the present invention will be fully understood and appreciated from the following detailed description of the accompanying Drawings.

BRIEF DESCRIPTION OF THE DRAWINGS

FIG. 1 is a perspective view of the testing apparatus for fixing and testing a LCD panel of the present invention;

DESCRIPTION OF THE PREFERRED EMBODIMENT

Figure 1:
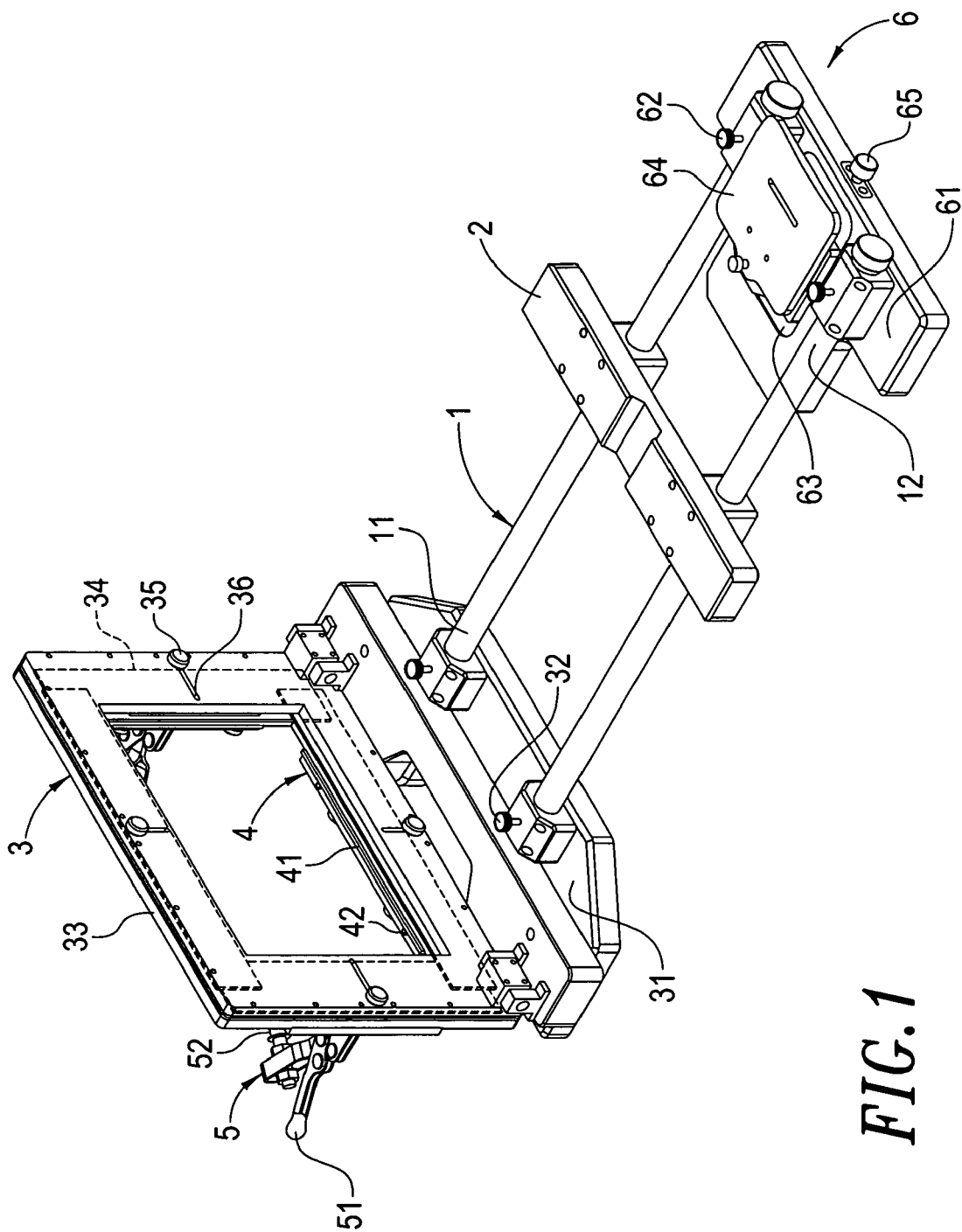
FIG. 1 is a perspective view of the solar-infrared-rays sensing garden lamp of the present invention.
Figure 2:
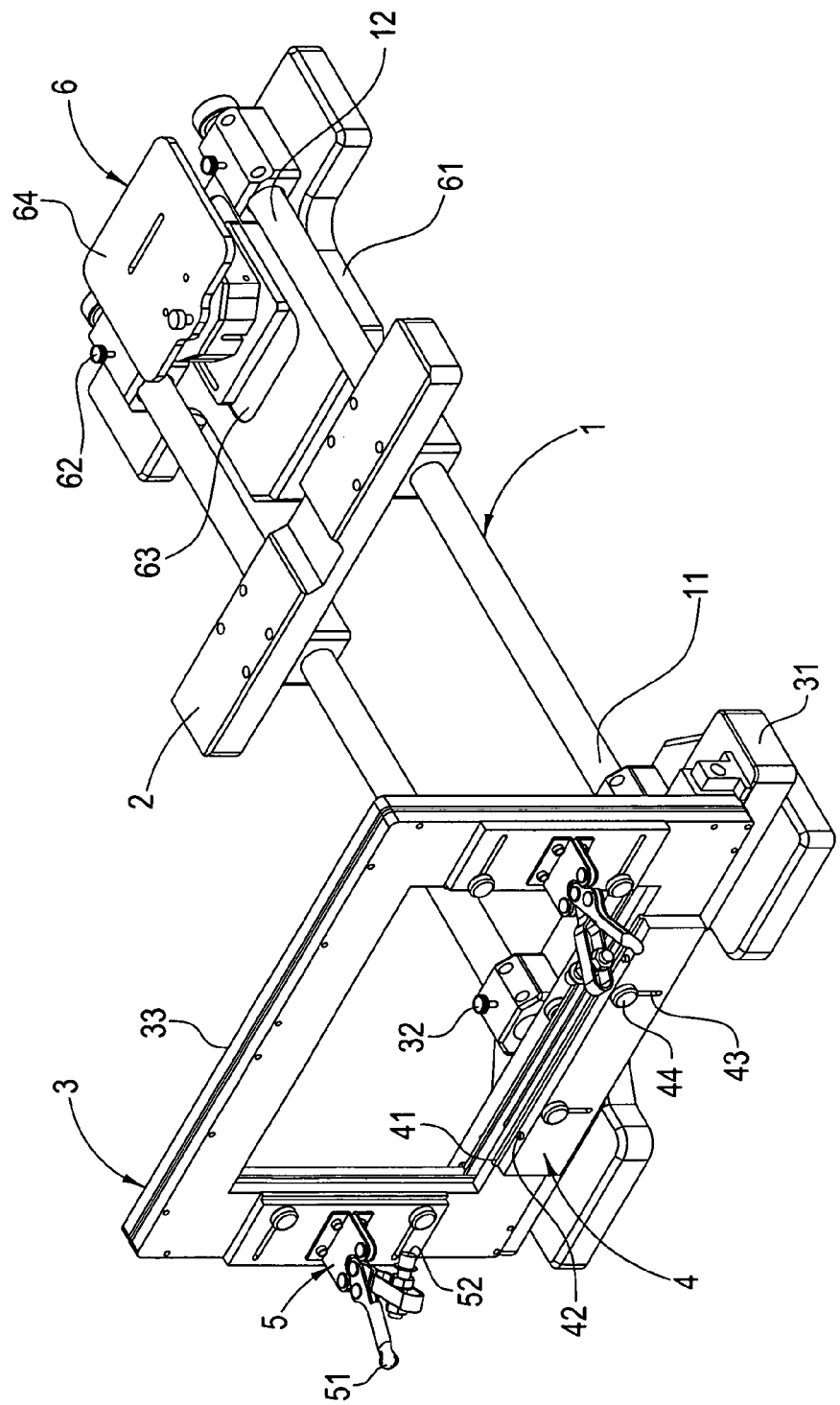
FIG. 2 is a perspective view the testing apparatus for fixing and testing a LCD panel of the present invention.
Figure 3A:
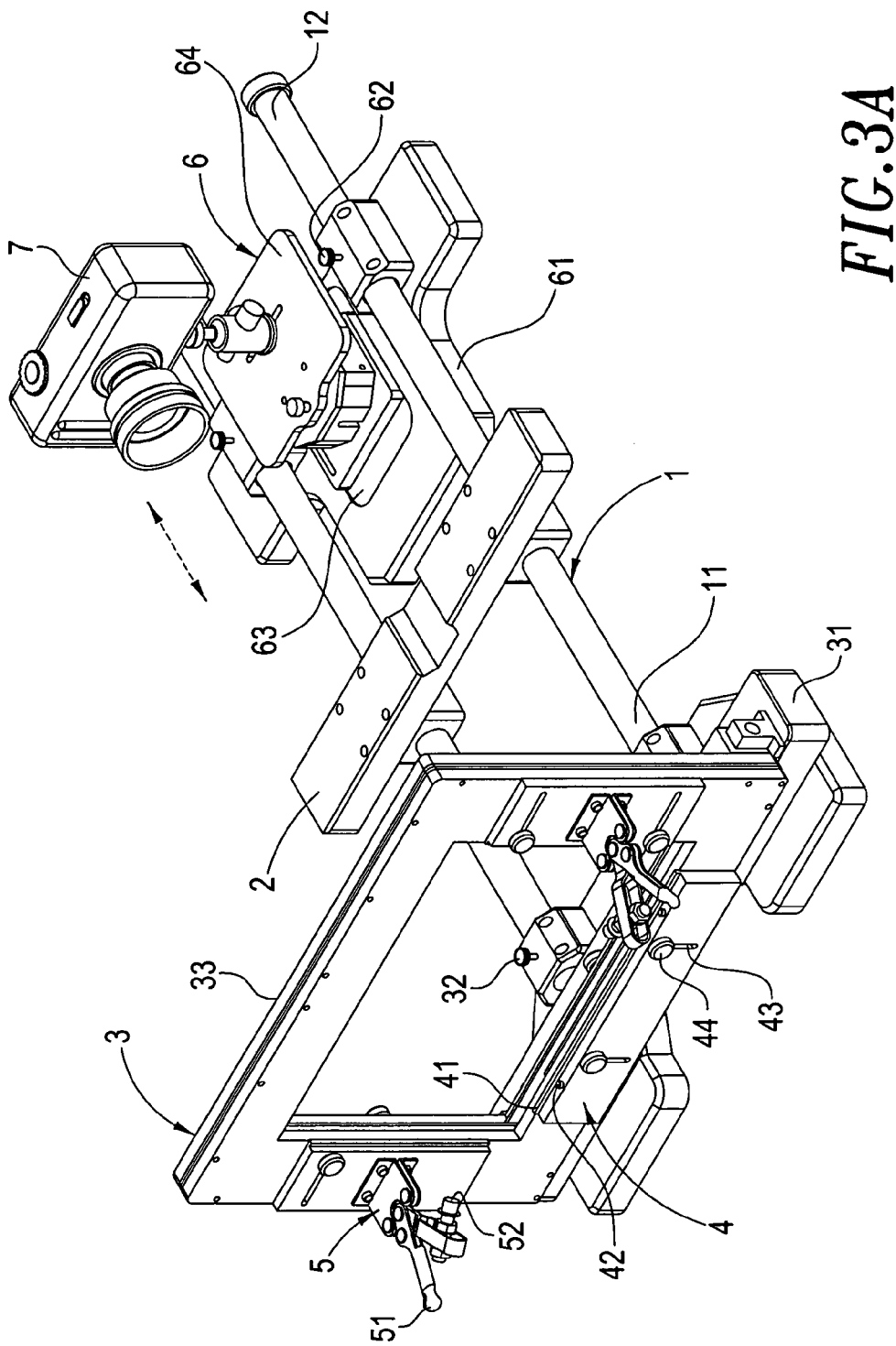
FIGS. 3A and 3B illustrate partial operation of the testing apparatus for fixing and testing a LCD panel of the present invention.
Figure 3B:
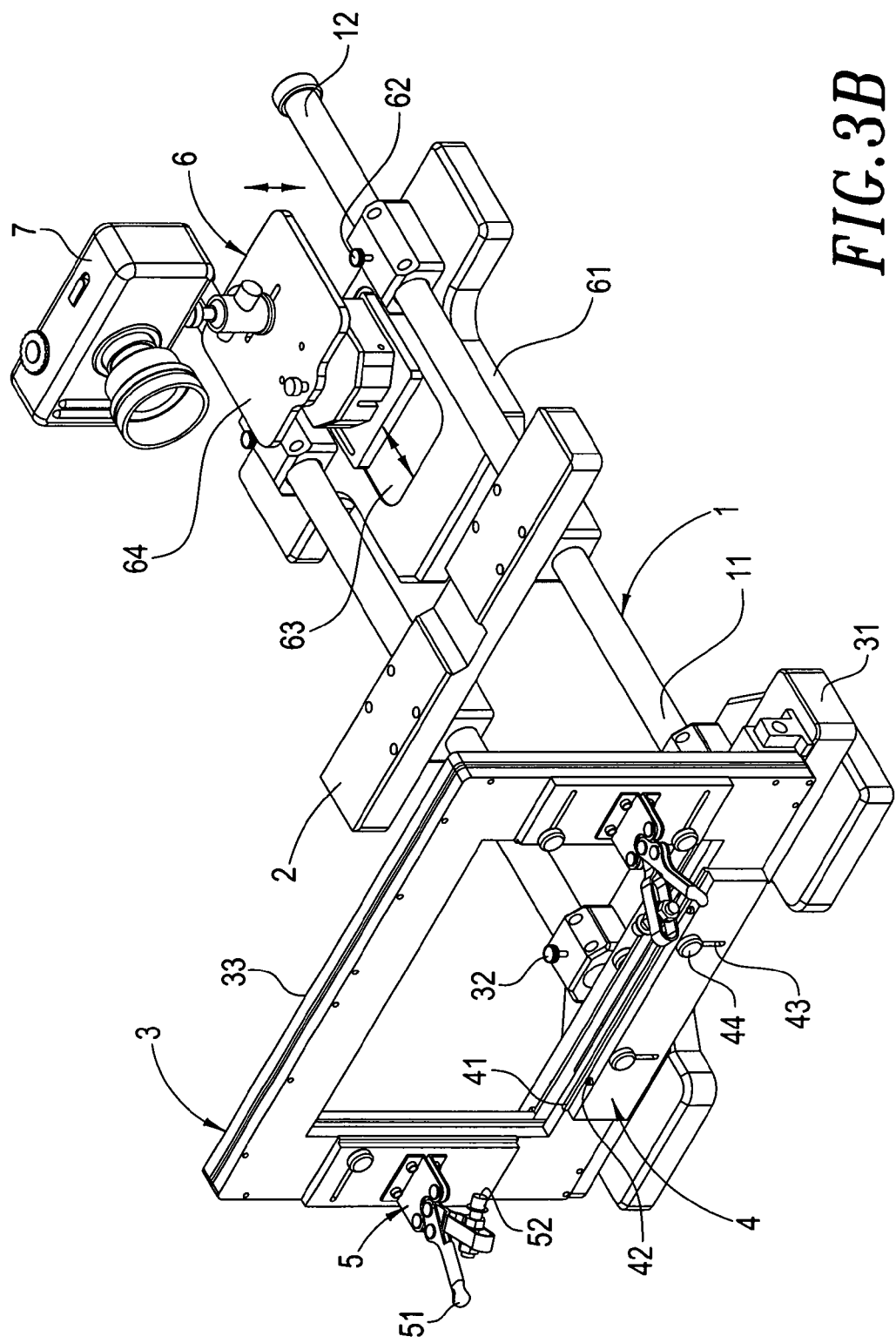
Figure 4A:
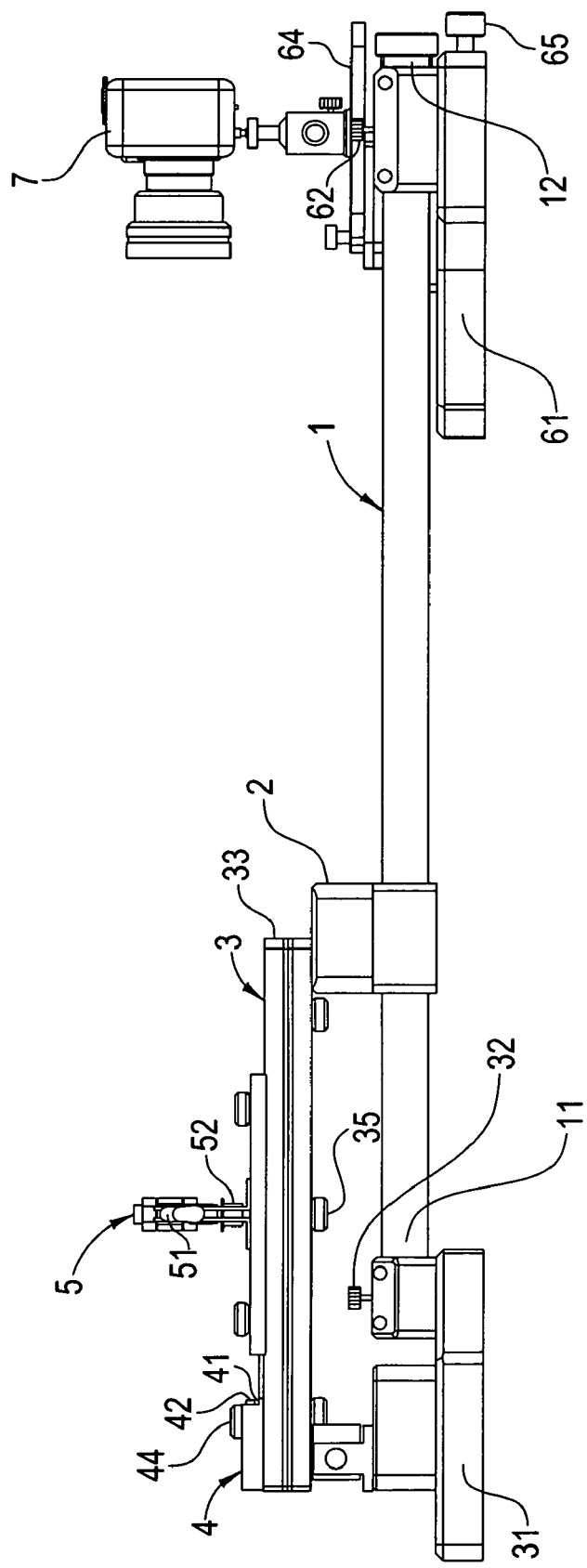
FIGS. 4A, 4B, 4C, 4D, 4E, and 4F illustrate operation of the testing apparatus for fixing and testing a LCD panel of the present invention.
Figure 4B:
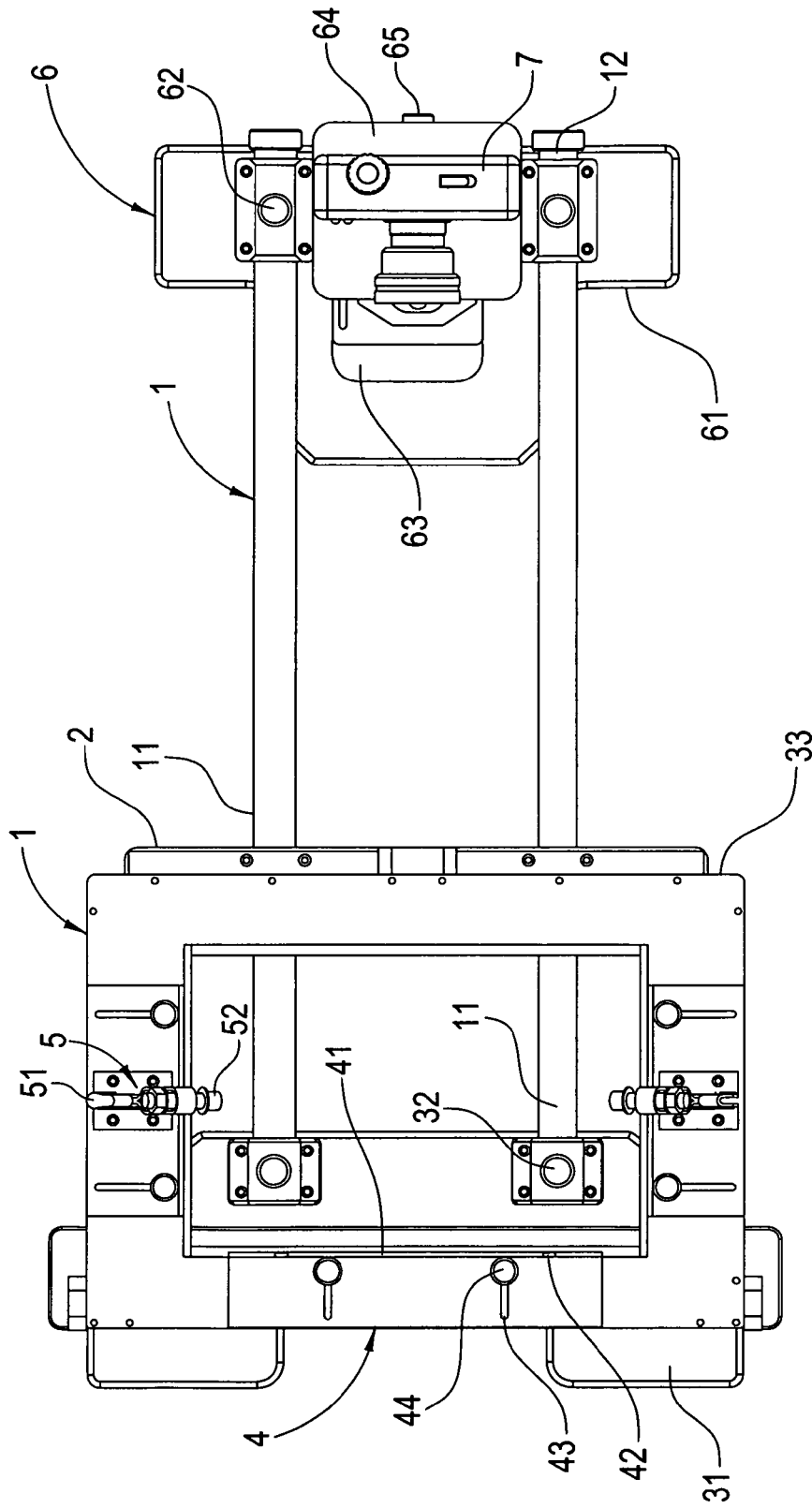
Figure 4C:
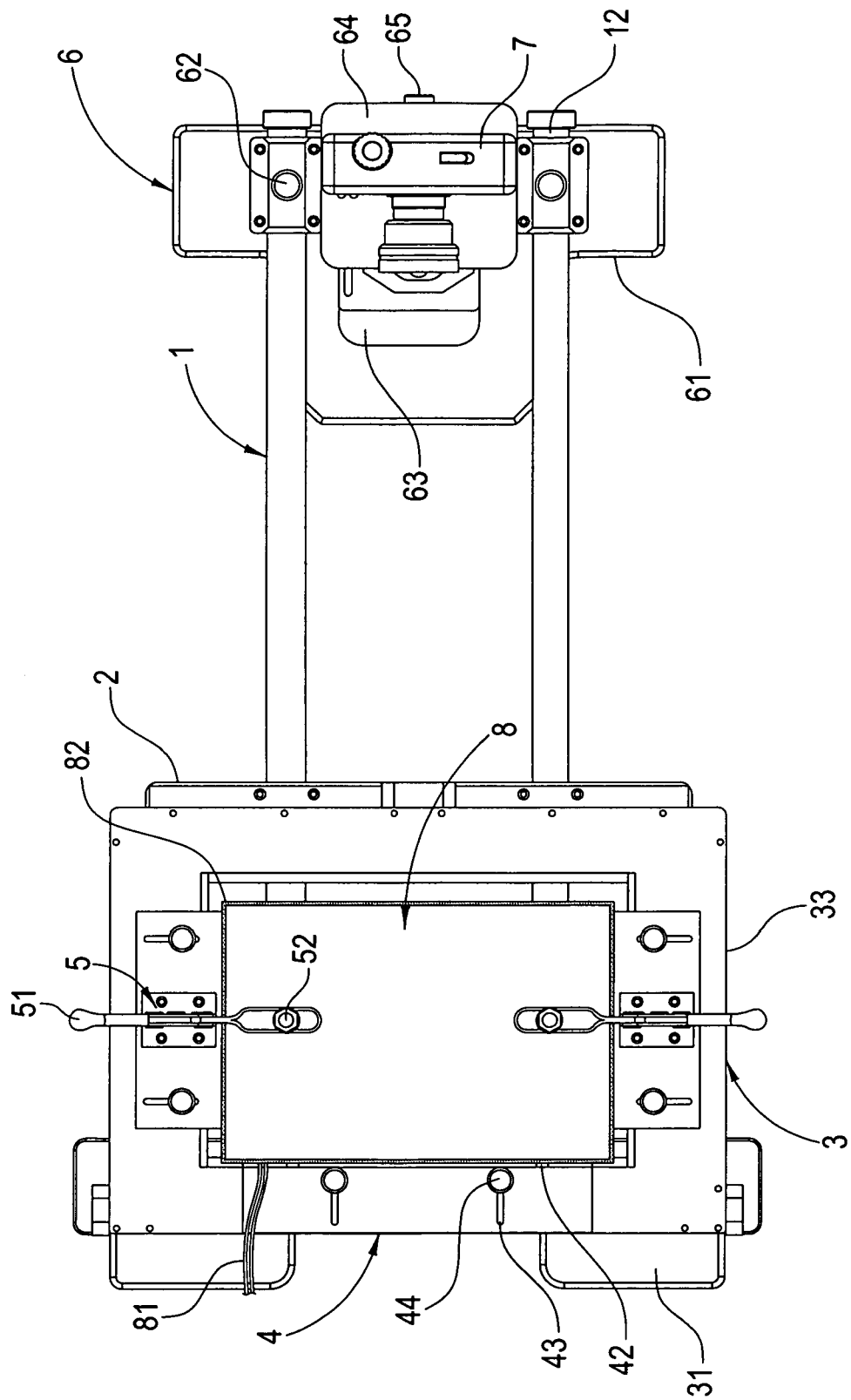
Figure 4D:
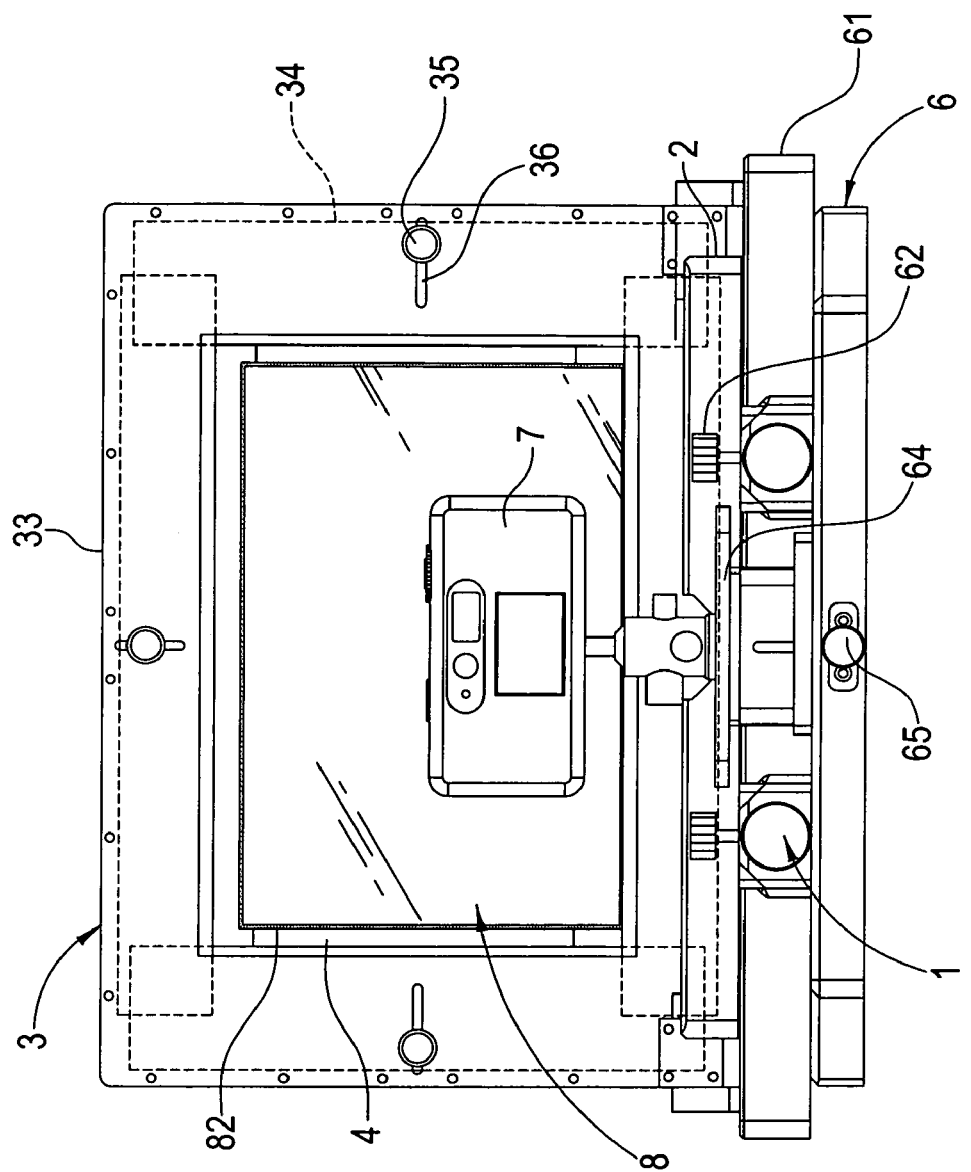
Figure 4E:
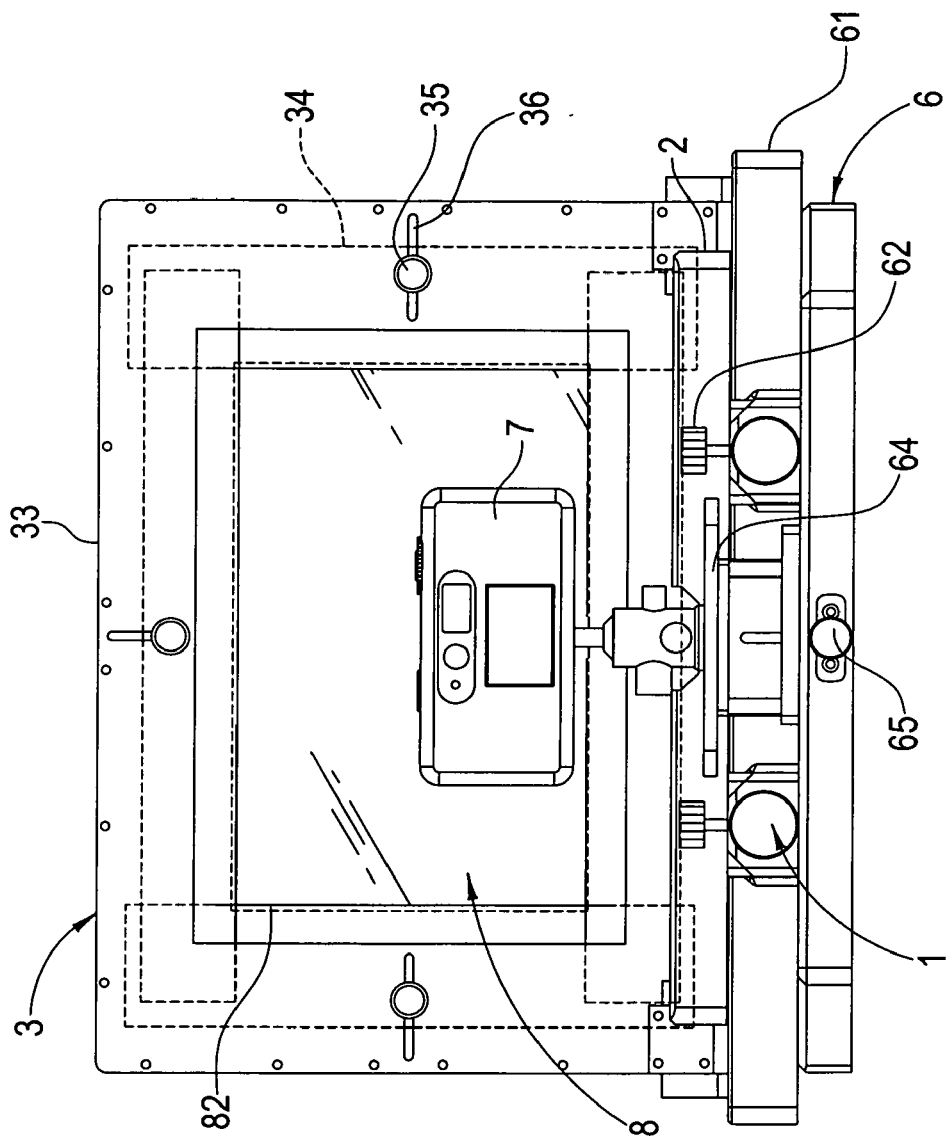
Figure 4F:
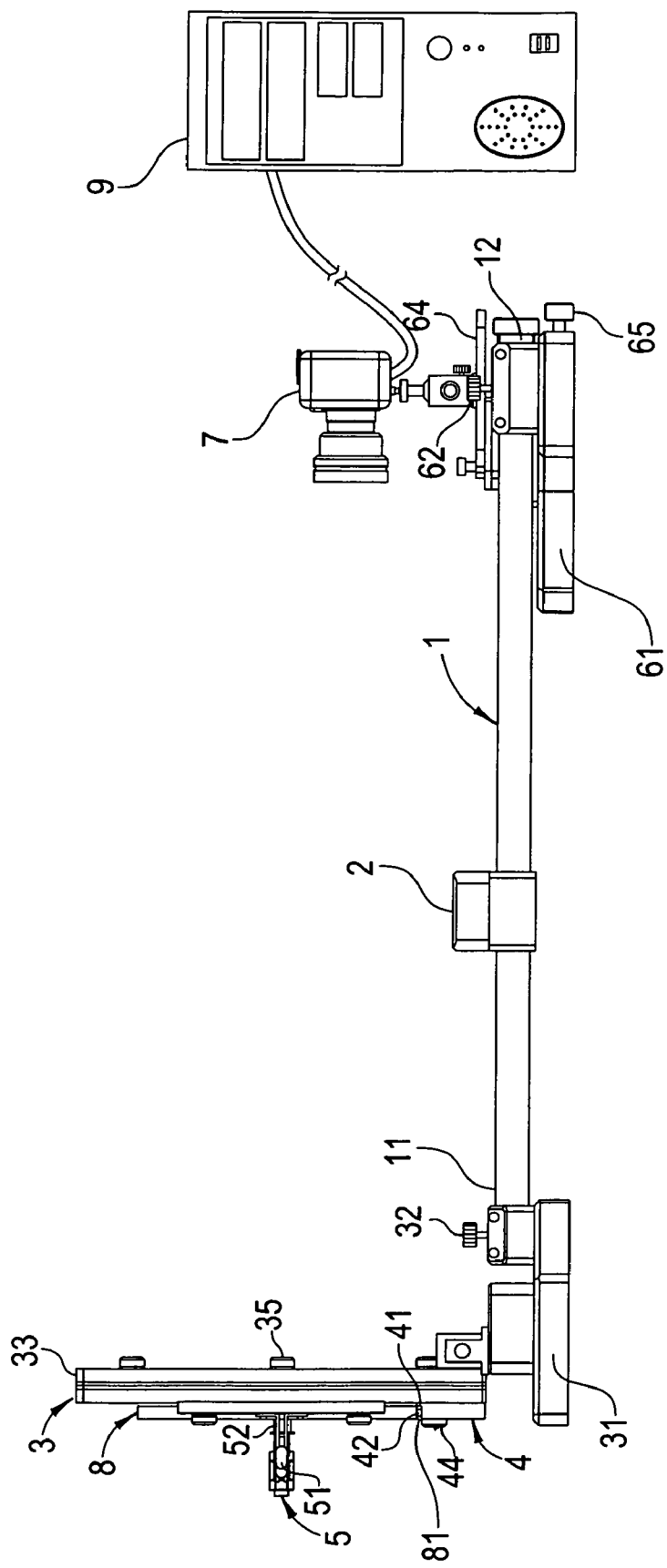

Refer to FIGS. 1 and 2, which show a testing apparatus for fixing and testing a LCD panel of the present invention mainly comprising:

a holder set 1, in which the holder set 1 comprises at least one axle pole, the holder set 1 comprises a first terminal 11 and a second terminal 12;

a supporting base 2, in which the supporting base 2 is set nearby the first terminal 11 on the holder set 1 and is able to move forward and backward along with the holder set 1;

a location frame 3, in which the location frame 3 comprises a position base 31, the position base 31 is set with a combination hole, a position screw 32 is set inside the combination hole, a framework 33 is pivoted to the top of the position base 31, the framework 33 can turn over downward from the position base 31, each backside of the bottom rim and back of the left and right rims of the framework 33 is fixed with an adjustable plate 4, a front edge of the top of the adjustable plate 4 extends with a wing 41, at least one protruding portion 42 is set on the top of the adjustable plate 4 of the backside of the bottom rim of the framework, the adjustable plate 4 is set with an adjustment opening 43, a fixing device 44 passes through the adjustment opening 43 for fixing the adjustable plate 4 on the backside of the framework 33, and the position of the adjustable plate 4 is adjusted by adjusting length of the adjustment opening 43, a top-supporting device 5 is fixed onto each of the adjustable plates 4 on the left and right rims, the top-supporting device 5 comprises a pressure pole 51 and an abutting device 52 being mutually pivoted together, the pressure pole 51 is configured to suppress down or lift up the abutting device 52, each rim of the framework 33 is internally set with a movable shade 34, the movable shade 34 is fixed with a control device 35 protruding outward the front of the framework 33, the control device 35 protrudes into the a groove 36 formed on the front of the framework 33 and is able to move along the groove 36 and to drive the movable shade 34 to move, the movable shade 34 is able to hide behind the rims of the framework 33 or protrude inward the framework 33;

the movable shade 34 is preferred to be black or in dark colors;

the combination hole of the position base 31 of the location frame 3 is configured to contain the first terminal 11 of the holder set 1, the position screw 32 is configured to fix the position base 31 on the holder set 1, the framework 33 is able to turn over toward the holder set 1 and abut the supporting base 2, the framework 33 is supported by the supporting base 2 and is parallel with the holder set 1;

an adjustable base 6, in which the adjustable base 6 comprises a foundation 61, the foundation 61 is set with a combination hole, a screw 62 is set inside the combination hole, an adjustment slot 63 is set on the top of the foundation 61, in which the adjustment slot 63 is combined with a placement base 64, the placement base 64 is connected to a lateral adjustment knob 65 set on the edge of the foundation 61, the lateral adjustment knob 65 is configured to adjust the lateral movement of the placement base 64 in the adjustment slot 63, and a vertical adjustment knob (not shown) is set on the placement base 64 for controlling the up and down movement of the placement base 64, the combination hole of the foundation 61 is configured to contain the second terminal 12 of the holder set 1 for moving the foundation 61 along the holder set 1 to a desired position, and the screw 62 is configured to fix the foundation 61 on the holder set 1.

Refer to FIGS. 3A, 3B, and 4A-4F, diagrams illustrating operation of the present invention are shown. In which, a camera set 7 is fixed on the placement base 64 of the adjustable base 6 and the camera set 7 corresponds to the position of the framework 33 of the location frame 3. Shooting focus of the camera set 7 is adjusted via moving the adjustable base 6 along the holder set 1. The lateral and vertical positions of the camera set 7 are fine tuned by tuning the lateral adjustment knob 65 and the vertical adjustment knob 65 respectively. Thus, the camera set 7 is able to accurately take image of the object on the framework 33 of the location frame 3.

When the LCD panel 8 is about to be fixed on the framework 33 of the location frame 3, the framework 33 of the location frame 3 is first turned over downward to make the framework 33 abut the position base 31, then the adjustable plates 4 are adjusted according to the size of the LCD panel 8 for placing the LCD panel 8 on the adjustable plates 4, in which the LCD panel 8 is supported by the wings 41 on the top of the adjustable plates 4. The screen of the LCD panel 8 faces toward the framework 33, and the bottom rim of the LCD panel 8 abuts the protruding portion 42 of the bottom adjustable plate 4 to retain a gap between the LCD panel 8 and the top of the bottom adjustable plate 4 for setting connection wires 81 of the LCD panel 8 and preventing the connection wires 81 from being compressed and bended. The pressure pole 51 of the top-supporting device 5 is pressured to suppress down the abutting device 52 to make the abutting device 52 abut the backside of the LCD panel 8 for locating the LCD panel 8 on the backside of the framework 33. Then the framework 33 is stood up to face the camera set 7. To prevent the camera set 7 from shooting the metal rims 82 of the LCD panel 8 and cause error determination of the testing module 9, it is able to make the movable shades 34 inside the four rims of the framework 33 protrude inward the framework 33 by adjusting the control device 35 on the front of the framework 33. Thus the movable shades 34 are able to shade the metal rims 82 of the LCD panel 8 to clearly define the boundaries of the screen area and the rims and to make the camera set 7 only take pictures of the serene area of the LCD panel 8. Then the pictures are transmitted to the testing module 9 for analyzing and determining quality.

The testing apparatus for fixing and testing a LCD panel of the present invention, comparing with other conventional technologies, is advantaged as follows.

1. The present invention is configured to fix the to-be-tested LCD panel on the location frame, then taking pictures of the LCD panel by the camera set on the adjustable base, thus, each picture is the same in size, and the pictures are transmitted to the testing module for analyzing and determining quality.

2. The present invention comprises adjustable plates on the location frame, thus the location frame is suitable for LCD panels with different sizes.

3. The present invention comprises the location frame with movable shades inside, and the movable shades are configured to shade the metal rims of the LCD panel to prevent the metal rims from influencing the analysis of product quality.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A testing apparatus for fixing and testing a LCD panel, comprising:

a holder set, having a first terminal and a second terminal;

a location frame, having a framework, in which the framework comprises at least two frame rims being combined with an adjustable plate on the back for moving forward and backward to adjust location position, a front edge of the top of the adjustable plate extends with a wing, a top-supporting device is fixed onto the adjustable plate, each rim of the framework is internally set with a movable shade, movement of the movable shade is controlled by each control device protruding outward each rim of the framework, and the location frame is fixed to the first terminal of the holder set; and an adjustable base, being fixed to the second terminal of the holder set, and being able to move forward and backward along the holder set, in which a camera set is able to be fixed on the adjustable base in response to the position of the framework of the location frame.

2. The testing apparatus for fixing and testing a LCD panel as claimed in claim 1, wherein the holder set comprises at least one axle pole.

3. The testing apparatus for fixing and testing a LCD panel as claimed in claim 1, wherein the adjustable plate is configured to be fixed on the bottom rim and back of the left and right rims of the framework, and at least one protruding portion is set on the top of the adjustable plate of the backside of the bottom rim of the framework to retain a gap between the LCD panel and the top of the adjustable plate for setting connection wires of the LCD panel.

4. The testing apparatus for fixing and testing a LCD panel as claimed in claim 1, wherein the location frame further comprises a position base pivoted to the framework, and the framework can turn over toward the holder set from the position base.

5. The testing apparatus for fixing and testing a LCD panel as claimed in claim 1, wherein the top-supporting device comprises a pressure pole and an abutting device being mutually pivoted together, the pressure pole is configured to suppress down or lift up the abutting device.

6. A testing apparatus for fixing and testing a LCD panel, comprising:
  a holder set, having a first terminal and a second terminal;
  a location frame, having a framework, in which the framework comprises at least two frame rims being combined with an adjustable plate on the back for moving along the backside of the frame rims to adjust location position, a wing extends from nearby a front edge of the top of the adjustable plate, a top-supporting device is fixed onto the adjustable plate, each rim of the framework is internally set with a movable shade, movement of the movable shade is controlled by each control device protruding outward each rim of the framework, and the location frame is fixed to the first terminal of the holder set; and
  an adjustable base, comprising a foundation set with an adjustment slot on the top thereof, in which the adjustment slot is combined with a placement base being able to move inside the adjustment slot vertically or laterally, the adjustable base being fixed to the second terminal of the holder set, and being able to move forward and backward along the holder set, in which a camera set is able to be fixed on the adjustable base in response to the position of the framework of the location frame.

7. The testing apparatus for fixing and testing a LCD panel as claimed in claim 6 further comprising a supporting base, in which the supporting base is set nearby the first terminal on the holder set and is able to move along with the holder set, when the framework of the location frame turns over toward the holder set, it is able to abut the supporting base.

8. The testing apparatus for fixing and testing a LCD panel as claimed in claim 6, wherein the adjustable plate is configured to be fixed on the bottom rim and back of the left and right rims of the framework, and at least one protruding portion is set on the top of the adjustable plate of the backside of the bottom rim of the framework to retain a gap between the LCD panel and the top of the adjustable plate for setting connection wires of the LCD panel.

9. The testing apparatus for fixing and testing a LCD panel as claimed in claim 6, wherein the position base of the location frame is set with a combination hole, a position screw is set inside the combination hole, the combination hole is configured to contain the first terminal of the holder set, and the position screw is configured to fix the position base on the holder set.

10. The testing apparatus for fixing and testing a LCD panel as claimed in claim 6, wherein the adjustable plate is set with an adjustment opening, a fixing device pass through the adjustment opening for fixing the adjustable plate on the backside of the framework, and the position of the adjustable plate is adjusted by adjusting length of the adjustment opening.

11. The testing apparatus for fixing and testing a LCD panel as claimed in claim 6, wherein the top-supporting device comprises a pressure pole and an abutting device being mutually pivoted together, the pressure pole is configured to suppress down or lift up the abutting device.

12. The testing apparatus for fixing and testing a LCD panel as claimed in claim 6, wherein the front of the rim of the framework is set with a groove, the groove is configured to be combined with a control device controlling the movement of the movable shade, the control device is able to move along the groove and drive the movable shade to move, thereby, the movable shade is able to hide behind the rims of the framework or protrude inward the framework.

13. The testing apparatus for fixing and testing a LCD panel as claimed in claim 6, wherein the foundation of the adjustable base is set with a combination hole, a screw is set inside the combination hole, the combination hole is configured to contain the second terminal of the holder set for moving the foundation along the holder set to a desired position, and the screw is configured to fix the foundation on the holder set.

14. The testing apparatus for fixing and testing a LCD panel as claimed in claim 6, wherein the foundation is set with a lateral adjustment knob on the edge, the lateral adjustment knob is configured to adjust the lateral movement of the placement base on the foundation.

\* \* \* \* \*